United States Patent [19]

Kohr

[11] Patent Number: 5,431,717
[45] Date of Patent: Jul. 11, 1995

[54] METHOD FOR RENDERING REFRACTORY SULFIDE ORES MORE SUSCEPTIBLE TO BIOOXIDATION

[75] Inventor: William J. Kohr, San Mateo, Calif.

[73] Assignee: Geobiotics, Inc., Hayward, Calif.

[21] Appl. No.: 161,742

[22] Filed: Dec. 3, 1993

[51] Int. Cl.$^6$ ............................................. B01D 53/00
[52] U.S. Cl. ............................... 75/744; 423/DIG. 17
[58] Field of Search ................. 75/744; 423/DIG. 17

[56] References Cited

U.S. PATENT DOCUMENTS

| 588,476 | 8/1897 | Rhodes . | |
|---|---|---|---|
| 3,777,004 | 12/1973 | Lankenau et al. | 423/20 |
| 3,819,797 | 6/1974 | Spedden et al. | 423/27 |
| 3,949,051 | 4/1976 | Pawlek | 423/28 |
| 4,017,309 | 4/1977 | Johnson | 75/101 |
| 4,056,261 | 11/1977 | Darrah | 266/101 |
| 4,256,705 | 3/1981 | Heinen et al. | 423/27 |
| 4,256,706 | 3/1981 | Heinen et al. | 423/29 |
| 4,279,868 | 7/1981 | Von Kohorn | 423/29 |
| 4,301,121 | 11/1981 | Von Kohorn | 423/1 |
| 4,318,892 | 3/1982 | Von Kohorn | 423/279 |
| 4,324,764 | 4/1982 | Hasegawa et al. | 422/159 |
| 4,343,773 | 8/1982 | Miller et al. | 423/1 |
| 4,374,097 | 2/1983 | Holland | 423/22 |
| 4,402,831 | 9/1983 | Beardsmore et al. | 210/606 |
| 4,424,194 | 1/1984 | Hughes | 423/1 |
| 4,526,615 | 7/1985 | Johnson | 75/101 |
| 4,557,905 | 12/1985 | Sherman et al. | 423/27 |
| 4,571,387 | 2/1986 | Bruynesteyn et al. | 435/262 |
| 4,585,548 | 4/1986 | Cadzow | 209/5 |
| 4,690,894 | 9/1987 | Brierley et al. | 435/244 |
| 4,721,526 | 1/1988 | Elmore et al. | 75/118 |
| 4,729,788 | 3/1988 | Hutchins et al. | 75/118 |
| 4,740,243 | 4/1988 | Krebs-Yuill et al. | 75/101 |
| 4,752,332 | 6/1988 | Wu et al. | 75/101 |
| 4,778,519 | 10/1988 | Pesic | 75/118 |
| 4,789,481 | 12/1988 | Brierley et al. | 210/661 |
| 5,127,942 | 7/1992 | Brierley et al. | 75/743 |
| 5,162,105 | 11/1992 | Kleid et al. | 423/29 |
| 5,196,052 | 3/1993 | Gross | 423/DIG. 17 |
| 5,232,676 | 8/1993 | Wolff | 423/DIG. 17 |
| 5,236,677 | 8/1993 | Torres-Cardona | 423/DIG. 17 |
| 5,244,493 | 9/1993 | Brierley | 423/DIG. 17 |
| 5,246,486 | 9/1993 | Brierly et al. | 75/743 |

OTHER PUBLICATIONS

Torma, A., *Mineral Bioprocessing*, Biomine '93 Conference, Mar. 22–23, 1993, Adelaide, South Africa, pp. 1.1–1.10.

Henley, K. J., et al., *The Mineralogy of Refractory Gold Ores*, Biomine '93 Conference, Mar. 22–23, 1993, Adelaide, South Africa, pp. 5.1–5.13.

Ritchie, A. I. M. et al., *Optimisation of Oxidation Rates in Dump Oxidation of Pyrite-Gold Ores*, Biomine '93 Conference, Mar. 22–23, 1993, Adelaide, South Africa, pp. 9.1–9.8.

Kelley, B. C. et al., *Bioremediation—Applications to Waste Processing in the Mining Industry*, Biomine '93 Conference, Mar. 22–23, 1993, Adelaide, South Africa, pp. 10.1–10.10.

Fraser, G. M., *Mixing and Oxygen Transfer in Mineral Bioleaching*, Biomine '93 Conference, Mar. 22–23, 1993, Adelaide, South Africa, pp. 16.1–16.11.

Nicholson, H., et al., *Selection of a Refractory Gold Treatment Process for the Sansu Project*, Biomine '93 Conference, Mar. 22–23, 1993, Adelaide, South Aafrica, pp. 20.1–20.11.

Untung, S. R., et al., *Application of Bio-Leaching to Some Indonesian Sulphide Ores (A Preliminary Study)*, Biomine '93 Conference, Mar. 22–23, 1993, Adelaide, South Africa, pp. 11.1–11.10.

(List continued on next page.)

*Primary Examiner*—Peter D. Rosenberg
*Attorney, Agent, or Firm*—Lyon & Lyon

[57] ABSTRACT

A method of recovering precious metal values from refractory sulfide ores is provided. The method includes the steps of separating clays and fines from a crushed refractory sulfide ore, forming a heap from the refractory sulfide ore, bioleaching the heap to thereby oxidize iron sulfides contained therein, and hydrometullurgically treating the bioleached ore to recover the precious metal values. If sufficient quantity of precious metal values are contained in the separated clays and fines, these materials can be further processed to recover the precious metal values contained therein.

11 Claims, No Drawings

OTHER PUBLICATIONS

Fraser, K. S. et al., *Processing of Refractory Gold Ores*, Minerals Engineering, vol. 4, Nos. 7–11, pp. 1029–1041, 1991.

Brierley, C. L., *Mineral Bio-Processing: Opportunities in Extractive Metallurgy and Environmental Control*, NIST, Nov. 1993, pp. 1–29.

Merson, J., *Mining With Microbes*, New Scientist, 4, Jan. 1991, pp. 17–19.

Browner, R. E., et al., *Studies on the Heap Leaching Characteristics of Western Australian Gold Ores*, World Gold (1991).

Mihaylov, B., et al., *Gold Recovery from a Low-Grade Ore Employing Biological Pretreatment in Columns*, Biohydrometallurgical Technologies, The Minerals, Metals & Materials Society (1993) pp. 499–511.

Brierly, J. A., et al., *Biooxidation–Heap Concept For Treatment of Refractory Gold Ore*, Biohydrometallurgical Technologies, The Minerals, Metals & Materials Society (1993) pp. 437–448.

Harrington, J. G., et al., *Engineering Aspects Of Heap Biooxidation Of Course–Crushed Refractory Gold Ores*, Biohydrometallurgical Technologies, The Minerals, Metals & Materials Society (1993) pp. 521–530.

Ahonen, L., et al., *Redox Potential–Controlled Bacterial Leaching Of Chalcopyrite Ores*, Biohydrometallurgical Technologies, The Minerals, Metals & Materials Society (1993) pp. 571–578.

Pantelis, G., et al., *Optimising Oxidation Rates In Heaps Of Pyritic Material*, Biohydrometallurgical Technologies, The Minerals, Metals & Materials Society (1993) pp. 731–738.

Mihaylov, B., et al.,*Biooxidation of A Sulfide Gold Ore in Columns*, Mineral Bioprocessing, The Minerals, Metals & Materials Society (1993) pp. 163–177.

Lizama, H. M., et al., *Bacterial Leaching Of Copper And Zinc From A Sulfide Ore By A Mixed Culture Of Thiobacillus Ferrooxidans And Thiobacillus Thiooxidans In Laboratory Scale And Pilot Plant Scale Columns*, Biohydrometallurgy (1989) pp. 519–531.

METHOD FOR RENDERING REFRACTORY SULFIDE ORES MORE SUSCEPTIBLE TO BIOOXIDATION

BACKGROUND OF THE INVENTION

1. Field of the Invention

The present invention relates to the recovery of metal values from refractory sulfide and refractory carbonaceous sulfide ores.

2. Description of the Prior Art

Gold is one of the rarest metals on earth. Gold ores can be categorized into two types: free milling and refractory. Free milling ores are those that can be processed by simple gravity techniques or direct cyanidation. Refractory ores, on the other hand, are not amenable to conventional cyanidation treatment. Such ores are often refractory because of their excessive content of metallic sulfides (e.g., pyrite) and/or organic carbonaceous matter.

A large number of refractory ores consist of ores with a precious metal such as gold occluded in iron sulfide particles. The iron sulfide particles consist principally of pyrite and arsenopyrite. Precious metal values are frequently occluded within the sulfide mineral. For example, gold often occurs as finely disseminated sub-microscopic particles within a refractory sulfide host of pyrite or arsenopyrite. If the gold remains occluded within the sulfide host, even after grinding, then the sulfides must be oxidized to liberate the encapsulated precious metal values and make them amenable to a leaching agent (or lixiviant).

A number of processes for oxidizing the sulfide minerals to liberate the precious metal values are well known in the art. One known method of oxidizing the metal sulfides in the ore is to use bacteria, such as *Thiobacillus ferrooxidans*, Sulfolobus, Acidianus species and facultative-thermophilic bacteria in a microbial pretreatment. The foregoing microorganisms oxidize the iron sulfide particles to cause the solubilization of iron as ferric iron, and sulfide, as sulfate ion.

If the refractory ore being processed is a carbonaceous sulfide ore, then additional process steps may be required following microbial pretreatment to prevent preg-robbing of the aurocyanide complex or other precious metal-lixiviant complexes by the native carbonaceous matter upon treatment with a lixiviant.

As used herein, sulfide ore or refractory sulfide ore will be understood to also encompass refractory carbonaceous sulfide ores.

A known method of bioleaching carbonaceous sulfide ores is disclosed in U.S. Pat. No. 4,729,788, issued Mar. 8, 1988, which is hereby incorporated by reference. According to the disclosed process, thermophilic bacteria, such as Sulfolobus and facultative-thermophilic bacteria, are used to oxidize the sulfide constituents of the ore. The bioleached ore is then treated with a blanking agent to inhibit the preg-robbing propensity of the carbonaceous component of the ore. The precious metals are then extracted from the ore using a conventional lixiviant of cyanide or thiourea.

Another known method of bioleaching carbonaceous sulfide ores is disclosed in U.S. Pat. No. 5,127,942, issued Jul. 7, 1992, which is hereby incorporated by reference. According to this method, the ore is subjected to an oxidative bioleach to oxidize the sulfide component of the ore and liberate the precious metal values. The ore is then inoculated with a bacterial consortium in the presence of nutrients therefor to promote the growth of the bacterial consortium, the bacterial consortium being characterized by the property of deactivating the preg-robbing propensity of the carbonaceous matter in the ore. In other words, the bacterial consortium functions as a biological blanking agent. Following treatment with the microbial consortium capable of deactivating the precious-metal-adsorbing carbon, the ore is then leached with an appropriate lixiviant to cause the dissolution of the precious metal in the ore.

Problems exist, however, with employing bioleaching processes in a heap leaching environment. These include nutrient access, air access, and carbon dioxide access for making the process more efficient and thus an attractive treatment option. Moreover, for biooxidation, the induction times concerning biooxidants, the growth cycles, viability of the bacteria and the like are important considerations because the variables such as accessibility, particle size, settling, compaction and the like are economically irreversible once a heap has been constructed. As a result, heaps cannot be repaired once formed, except on a limited basis.

Ores that have a high clay and/or fines content are especially problematic when processing in a heap leaching or heap biooxidation process. The reason for this is that the clay and/or fines can migrate through the heap and plug channels of air and liquid flow, resulting in puddling; channelling; nutrient-, carbon dioxide-, or oxygen-starving; uneven biooxidant distribution, and the like. As a result, large areas of the heap may be blinded off and ineffectively leached. This is a common problem in cyanide leaching and has lead to processes of particle agglomeration with cement for high pH cyanide leaching and with polymers for low pH biooleaching. Polymer agglomerate aids may also be used in high pH environments, which are customarily used for leaching the precious metals, following oxidative bioleaching of the iron sulfides in the ore.

Biooxidation of refractory sulfide ores is especially sensitive to blocked percolation channels by loose clay and fine material because the bacteria need large amounts of air or oxygen to grow and biooxidize the iron sulfide particles in the ore. Air flow is also important to dissipate heat generated by the exothermic biooxidation reaction, because excessive heat can kill the growing bacteria in a large, poorly ventilated heap.

SUMMARY OF INVENTION

It is an object of the present invention to provide a heap bioleaching process of the type described above, wherein the refractory sulfide ore is rendered more susceptible to biooxidation, thereby providing improved recovery of the precious metal values contained within the ore. The method of the present invention achieves this object by removing the clays and/or fines from the refractory sulfide ore after it is crushed to a size appropriate for a heap leaching process. The heap may then be formed without concern of the air and liquid flow channels in the heap becoming plugged. Further, if the separated clay and/or fine material has a sufficiently high precious metal content, it may be separately treated to recover the precious metal values contained therein.

The above and other objects, features and advantages will become apparent to those skilled in the art from the following description of the preferred embodiments.

DESCRIPTION OF THE PREFERRED EMBODIMENTS

By the method according to the present embodiment of the invention, refractory sulfide ores can be rendered more susceptible to biooxidation in a heap leaching process. This is accomplished by separating the clay and/or fine materials from the refractory sulfide ore after it has been crushed to a size appropriate for heap leaching. In the present embodiment the method of removal is wet size screening. It will be readily apparent to those skilled in the art, however, that any other method for separating the clay and/or fine material from the refractory ore may be used. For example, dry screening and cyclone classifying are well known to those skilled in the art.

By removing the fines and clays from the refractory sulfide ore, the air and liquid flow through the heap is improved. This will reduce the time required to sufficiently biooxidize the iron sulfide particles in the ore to liberate the precious metal values and make them amenable to subsequent lixiviation with cyanide or thiourea, preferably cyanide. In addition to faster biooxidation, in a well ventilated heap, having good fluid flow, it becomes more feasible to change the pH from an acidic pH of 1.0 to 2.0 that is best for biooxidation to a basic pH of 10.0 or more needed for cyanide leaching without remaking or restacking the heap.

The refractory sulfide ore is preferably crushed to a target maximum size in the range of approximately $\frac{1}{4}$ to 1 inch. Appropriate target maximum particle sizes include $\frac{1}{4}$, $\frac{3}{8}$, $\frac{1}{2}$, and 1 inch. If the ore will pass any of these target particle sizes, it should be amenable to heap leaching. The smaller the particle size, however, the greater the surface area of the sulfide particles in the ore and, of course, the faster the sulfide particles will be biooxidized. Increased recovery of the precious metal values should also result. This, however, must be weighed against the additional cost of crushing the ore to a smaller particle size. The additional amount of precious metal recovered may not justify the added cost.

Of course if the refractory sulfide ore body being treated is already an appropriate size for heap leaching, no additional crushing is required.

Fines are naturally produced during the crushing process. The size of the fines and clays removed from the crushed ore should be about minus 60 mesh as a minimum upper limit to about minus to $\frac{1}{8}$ inch as a maximum upper limit. After the clay and fines are separated from the bulk of the ore, a heap is formed with the ore. The heap may then be treated with a standard bioleaching process to oxidize the iron sulfide particles in the ore and liberate the occluded precious metal values, which are preferably gold. Because the majority of the clay and fine materials have been removed, obstruction of the air and liquid flow channels by these materials is no longer a concern, thereby improving percolation leaching of the ore.

After biooxidation, the precious metal in the pretreated ore can be extracted using a conventional lixiviant such as cyanide or thiourea, preferably cyanide. Of course, however, as a person of ordinary skill in the art would recognize, if the refractory sulfide ore is also refractory due to carbonaceous matter contained in the ore, additional processing steps must be employed to reduce the preg-robbing propensity of the ore prior to lixiviation. A number of such processes are well known in the art.

For example, the methods used in U.S. Pat. No. 4,729,788 and U.S. Pat. No. 5,127,942, both of which have already been incorporated herein by reference, can be used. Further, the microbial process for treating carbonaceous ores disclosed in U.S. Pat. No. 5,162,105, issued Nov. 10, 1992, hereby incorporated by reference, can also be used.

The fine material that has been separated may contain large amounts of precious metal values. Indeed the economic value of these metal values may be sufficiently high to justify further processing of these materials to recover the additional metal values. In a particularly preferred embodiment of the present invention, the separated fine material is further processed to recover at least a portion of the precious metal values contained therein.

To recover the precious metal values from the fine material, the fine material is preferably treated in a mill process to remove the iron sulfide particles from the clay and sand particles. The reason for this is that, as discussed above, precious metal values, especially gold, often occur as finely disseminated microscopic particles within the iron sulfide particles. These fine sulfide particles, therefore, frequently contain a significant portion of the overall precious metal values. Further, because a relatively high percentage of the precious metal values in the ore are associated with this fraction of the ore, they can be economically treated in a mill process.

As will be recognized by those skilled in the art, a variety of methods can be used to separate the iron sulfide particles from the remainder of the fines. These methods include, by way of example only, gravity separation and flotation. If desired, the iron sulfide particles can be subjected to additional grinding before flotation.

The iron sulfide concentrate, if refractory, is preferably bioleached with bacteria in a tank or mill process to liberate the occluded precious metal values. Alternatively, the sulfide concentrate can be added back to the heap to allow for a slower heap biooxidation process. However, because these particles are typically larger and more hydrophobic than clay particles, they tend to stick more readily to the larger particles in the heap, and, thus, the problem of obstructed percolation channels is not encountered. The iron sulfide concentrate can also be treated by a variety of other methods well known in the art such as roasting, pressure oxidation, and chemical oxidation. Because the concentration of gold or other precious metal values is relatively high in this ore fraction and its overall volume small, all of these mill processes may be economically utilized.

If the iron sulfide concentrate is only partially refractory, then it can be directly leached with a lixiviant such as cyanide to remove the nonrefractory gold. The tail from this leaching process could then be washed free of cyanide and added to the heap for biooxidation to release the remaining refractory gold or other precious metal values.

The fine material removed from the refractory sulfide ore by size separation, and which has also had the iron sulfide particles removed from it, may still contain economic values of gold or other precious metals. Further, this fine material is likely to be less refractory than other iron sulfide material if its size has lead to oxidation. Therefore, agglomeration of this material with cement, or other agglomeration aids that can be used at a high pH, may provide good recoveries if leached with cyanide directly.

EXAMPLE 1

A sample of 16 kg of refractory sulfide ore with approximately 0.04 oz/ton of gold and 3.5% of sulfide sulphur was crushed to $-\frac{1}{4}$ inch. The ore sample was then separated by wet screening into a $+-\frac{1}{8}$ to $-\frac{1}{4}$ inch, a $-30$ mesh to $-\frac{1}{8}$ inch, and a $-30$ mesh material fractions. The $-30$ mesh material was further separated into a pyrite fraction, a sand fraction, and a clay fraction by gravity separation. The sand fraction was further processed by fine grinding in a ball mill for about one hour. This material was then floated with xanthate as a collector.

Each fraction was then dried and weighed and analyzed for gold. The $+\frac{1}{8}$ to $-\frac{1}{4}$ inch material represented 51% of the weight and 18% of the gold at 0.48 ppm Au. The $+30$ mesh to $-\frac{1}{8}$ inch material represented 28% of the weight and 32% of the gold at 1.47 ppm Au. The total pyrite, which included both the gravity separated pyrite and the pyrite concentrate from the flotation of the sand, represented 4.7% of the weight and 35% of the gold at 9.8 ppm Au. The remaining sand flotation tail and clay material represented 16% of the weight and 14.6% of the gold at about 1.2 ppm Au.

The $+\frac{1}{8}$ to $-\frac{1}{4}$ inch material and the $+30$ mesh to $-\frac{1}{8}$ inch material were combined according to their weight percentages. The combined material was adjusted to a pH of 2.0 with 10% sulfuric acid at 30 ml/kg. The one mixture was then poured into a column and aerated from the bottom with at least 15 of air/min/m$^2$ and liquid dilute basal solutions of (NH$_4$)$_2$SO$_4$ 0.04 g/l MgSO$_4$·7H$_2$ at 0.04 g/l and KH$_2$PO$_4$ at 0.004 g/l were added to the top at about 15 ml/hour. Thiobacillus ferrooxidans bacteria was added to the top of the column and washed into the column with the liquid flow. This procedure allowed for good air flow and liquid flow and also migration of bacteria through the column. After about one month the effluent from the column showed good bioleaching of iron at about 0.1% per day.

Although the invention has been described with reference to preferred embodiments and specific examples, it will readily be appreciated by those of ordinary skill in the art that many modifications and adaptions of the invention are possible without departure from the spirit and scope of the invention as claimed hereinafter. For example, while the processes according to the present invention have been described in terms of recovering gold from refractory sulfide or refractory carbonaceous sulfide ores, the processes are equally applicable to other precious metals found in these ores such as silver and platinum.

I claim:

1. A method for recovering precious metal values from refractory sulfide ores, comprising:
   a. separating fines from a crushed refractory sulfide ore;
   b. forming a heap with said refractory sulfide ore;
   c. bioleaching said heap to thereby oxidize iron sulfides contained therein;
   d. hydrometallurgically treating the bioleached ore to recover the precious metal values; and
   e. treating the separated fines to recover precious metal values contained therein.

2. A method according to claim 1, further comprising: treatment comprises:
   a. separating precious metal containing iron sulfide particles from the fines;
   b. oxidizing said iron sulfide particles;
   c. hydrometallurgically treating said oxidized precious metal containing iron sulfide particles to recover the precious metal values.

3. A method according to claim 1, wherein said method of treatment comprises:
   a. separating precious metal containing iron sulfide particles from the fines;
   b. hydrometallurgically treating said iron sulfide particles to recover nonrefractory precious metal values;
   c. oxidizing said iron sulfide particles; and
   d. hydrometallurgically treating said oxidized iron sulfide particles to recover additional precious metal values.

4. A method according to claim 2, further comprising:
   a. agglomerating the fines after separation of said iron sulfide particles; and
   b. hydrometallurgically treating said agglomerated fines to recover precious metal values.

5. A method according to claim 3, further comprising:
   a. agglomerating the fines after separation of said iron sulfide particles; and
   b. hydrometallurgically treating said agglomerated fines to recover precious metal values.

6. A method according to claim 1, wherein said hydrometallurgical treatment comprises leaching said heap with a lixiviant selected from the group consisting of cyanide and thiourea.

7. A method according to claim 1, wherein said crushed refractory sulfide ore has a maximum particle size in the range of approximately $\frac{1}{4}$ inch to 1 inch, and said fines have a maximum particle size of about $-60$ mesh to $-\frac{1}{8}$ inch.

8. A method according to claim 1, wherein the recovered precious metal is at least one metal selected from the group consisting of gold, silver, and platinum.

9. A method according to claim 1, wherein the recovered precious metal is gold.

10. A method according to claim 2, wherein said separated iron sulfide particles are oxidized by biooxidation.

11. A method according to claim 3, wherein said separated iron sulfide particles are oxidized by biooxidation.

* * * * *